(12) United States Patent
Knodel

(10) Patent No.: US 8,926,658 B1
(45) Date of Patent: Jan. 6, 2015

(54) ENDOCUTTER WITH AUTO-FEED BUTTRESS

(71) Applicant: Cardica, Inc., Redwood City, CA (US)

(72) Inventor: Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 272 days.

(21) Appl. No.: 13/645,416

(22) Filed: Oct. 4, 2012

Related U.S. Application Data

(62) Division of application No. 12/381,316, filed on Mar. 9, 2009, now Pat. No. 8,317,071.

(51) Int. Cl.
*A61D 1/00* (2006.01)

(52) U.S. Cl.
USPC ....................................... 606/219

(58) Field of Classification Search
CPC ............ A61B 17/0644; A61B 17/064; A61B 2017/00004; A61B 17/07207; A61B 17/115; A61B 17/0643; A61B 2017/0647; A61B 17/068; A61B 17/083; A61B 17/08; A61B 17/085; A61B 2017/06076
USPC ................ 606/219–221, 151, 215; 227/175.1
See application file for complete search history.

(56) References Cited

U.S. PATENT DOCUMENTS

| | | |
|---|---|---|
| 3,581,551 A | 6/1971 | Wilkinson |
| 3,650,453 A | 3/1972 | Smith, Jr. |
| 3,899,914 A | 8/1975 | Akiyama |
| 4,086,926 A | 5/1978 | Green et al. |
| 4,228,895 A | 10/1980 | Larkin |
| 4,475,679 A | 10/1984 | Fleury, Jr. |
| 4,633,861 A | 1/1987 | Chow et al. |
| 4,762,260 A | 8/1988 | Richards et al. |
| 4,969,591 A | 11/1990 | Richards et al. |
| 5,156,315 A | 10/1992 | Green et al. |
| 5,192,288 A | 3/1993 | Thompson et al. |
| 5,413,272 A | 5/1995 | Green et al. |

(Continued)

FOREIGN PATENT DOCUMENTS

| | | |
|---|---|---|
| EP | 1238634 | 9/1994 |
| JP | 2005160933 | 6/2005 |

(Continued)

OTHER PUBLICATIONS

"Cardica Microcutter Implant Delivery Device 510(k), Cover Sheet, Table 10.1, "Substantial Equivalence Comparison", and Section 12, "Substantial Equivalence Discussion"".

(Continued)

*Primary Examiner* — Katherine Dowe
*Assistant Examiner* — Amy Shipley
(74) *Attorney, Agent, or Firm* — Cardica, Inc.

(57) ABSTRACT

A surgical method of treating tissue within the body of a patient may include: providing an endocutter having a staple holder and a plurality of staples, where a plurality, but less than all, of the staples are arranged in a firing position within the staple holder; engaging tissue of the patient with the staple holder; deploying the plurality of staples in firing position through a buttress and into tissue of the patient; disengaging the end effector from tissue of the patient; moving a plurality of staples into firing position; engaging tissue of the patient with the staple holder; advancing a segment of buttress relative to the staple holder; and repeating the deploying.

4 Claims, 1 Drawing Sheet

(56) References Cited

U.S. PATENT DOCUMENTS

| | | | |
|---|---|---|---|
| 5,476,206 A | 12/1995 | Green | |
| 5,549,628 A * | 8/1996 | Cooper et al. | 606/220 |
| 5,655,698 A | 8/1997 | Yoon | |
| 5,662,260 A | 9/1997 | Yoon | |
| 5,692,668 A | 12/1997 | Schulze et al. | |
| 5,810,855 A | 9/1998 | Rayburn et al. | |
| 5,816,471 A | 10/1998 | Plyley et al. | |
| 5,855,311 A | 1/1999 | Hamblin et al. | |
| 5,894,979 A | 4/1999 | Powell | |
| 5,918,791 A | 7/1999 | Sorrentino et al. | |
| 5,964,774 A * | 10/1999 | McKean et al. | 606/151 |
| 6,063,097 A * | 5/2000 | Oi et al. | 606/151 |
| 6,306,149 B1 | 10/2001 | Meade | |
| 6,391,038 B2 | 5/2002 | Vargas et al. | |
| 6,503,257 B2 * | 1/2003 | Grant et al. | 606/151 |
| 6,592,597 B2 * | 7/2003 | Grant et al. | 606/151 |
| 6,602,252 B2 | 8/2003 | Mollenauer | |
| 6,716,232 B1 | 4/2004 | Vidal et al. | |
| 6,817,508 B1 | 11/2004 | Racenet et al. | |
| 6,843,403 B2 | 1/2005 | Whitman | |
| 7,025,747 B2 | 4/2006 | Smith | |
| 7,097,089 B2 | 8/2006 | Marczyk | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 * | 7/2007 | Viola | 606/219 |
| 7,845,533 B2 * | 12/2010 | Marczyk et al. | 227/175.1 |
| 8,317,071 B1 * | 11/2012 | Knodel | 227/175.1 |
| 2003/0120284 A1 | 6/2003 | Palacios et al. | |
| 2003/0236551 A1 | 12/2003 | Peterson | |
| 2005/0184121 A1 | 8/2005 | Heinrich | |
| 2006/0011699 A1 | 1/2006 | Olson et al. | |
| 2006/0041273 A1 | 2/2006 | Ortiz et al. | |
| 2006/0151567 A1 | 7/2006 | Roy | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0118163 A1 | 5/2007 | Boudreaux et al. | |
| 2007/0125828 A1 | 6/2007 | Rethy et al. | |

FOREIGN PATENT DOCUMENTS

| | | |
|---|---|---|
| RU | 2080833 | 6/1997 |
| WO | WO-81/01953 | 7/1981 |
| WO | WO-85/01427 | 4/1985 |

OTHER PUBLICATIONS

Gong, Shao W., "Perfectly flexible mechanism and integrated mechanism system design", *Mechanism and Machine Theory 39* (2004), (Nov. 2004),1155-1174.

Kolios, Efrossini et al., "Microlaparoscopy", *J. Endourology 18(9)*, (Nov. 2004),811-817.

Lim, Jonas J., et al., "Application of Type Synthesis Theory to the Redesign of a Complex Surgical Instrument", *Journal of Biomechanical Engineering* (124), (Jun. 2004),265-272.

Lim, Jonas J., et al., "A review of mechanism used in laparascopic surgical instruments", *Mechanism and Machine Theory 38*, (2003),1133-1147.

Lim, Jyue B., "Type Synthesis of a Complex Surgical Device", *Masters Thesis*, (Feb. 21, 2001).

Steichen, Felicien M., et al., "Mechanical Sutures in Surgery", *Brit. J. Surg. 60(3)*, (Mar. 1973), 191-197.

* cited by examiner

ENDOCUTTER WITH AUTO-FEED BUTTRESS

CROSS REFERENCE TO RELATED APPLICATIONS

This application is a divisional of application Ser. No. 12/381,316, filed Mar. 9, 2009, now U.S. Pat. No. 8,317,071 which is hereby incorporated herein by reference in its entirety and from which priority is hereby claimed under 35 U.S.C. §120.

FIELD OF THE INVENTION

The invention generally relates to a surgical tool and method, and more specifically to an endocutter utilizing buttress material.

BACKGROUND

An endocutter is a surgical tool that staples and cuts tissue to transect that tissue while leaving the cut ends hemostatic. An endocutter is small enough in diameter for use in minimally invasive surgery, where access to a surgical site is obtained through a trocar, port, or small incision in the body. A linear cutter is a larger version of an endocutter, and is used to transect portions of the gastrointestinal tract. A typical endocutter receives at its distal end a disposable single-use cartridge with several rows of staples, and includes an anvil opposed to the cartridge. The surgeon inserts the endocutter through a trocar or other port or incision in the body, orients the end of the endocutter around the tissue to be transected, and compresses the anvil and cartridge together to clamp the tissue. Then, a row or rows of staples are deployed on either side of the transection line, and a blade is advanced along the transection line to divide the tissue.

An endocutter, or other surgical stapler, is sometimes utilized to treat tissue that is friable, diseased, or otherwise in a weakened condition. A buttress is known to be used in conjunction with a surgical stapler in order to distribute the force exerted by contact between the staple back and tissue across a greater amount of tissue, thereby decreasing the load on fragile tissue. However, no buttress delivery system is known for a true multi-fire surgical instrument that is capable of firing multiple groups of staples into tissue without the need to exchange cartridges or remove the staple holder from the patient.

BRIEF DESCRIPTION OF THE DRAWINGS

The use of the same reference symbols in different figures indicates similar or identical items.

DETAILED DESCRIPTION

Figure 1:
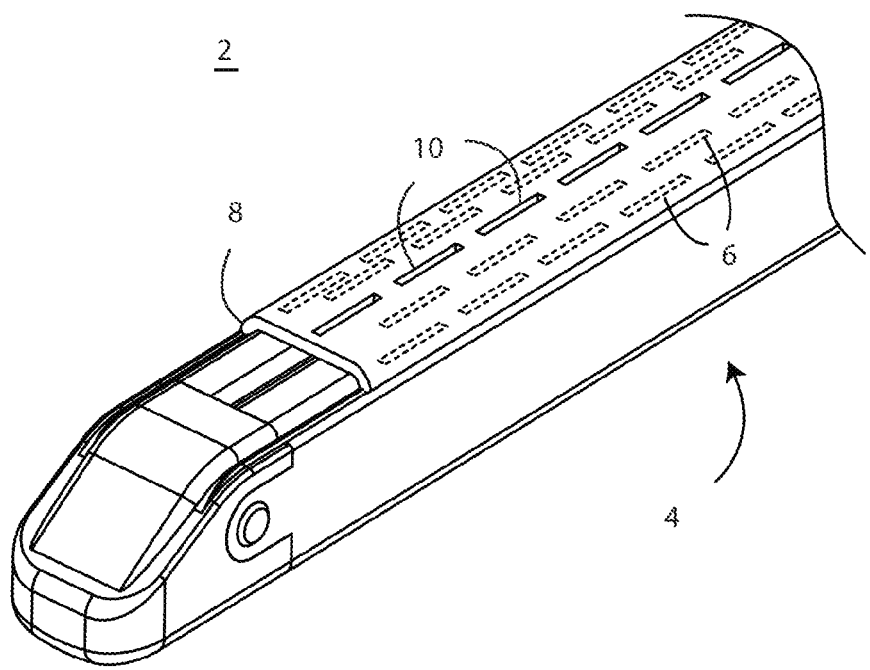
FIG. 1 is a perspective view of the staple holder of an endocutter configured to automatically feed a segment of buttress material.
Figure 2:
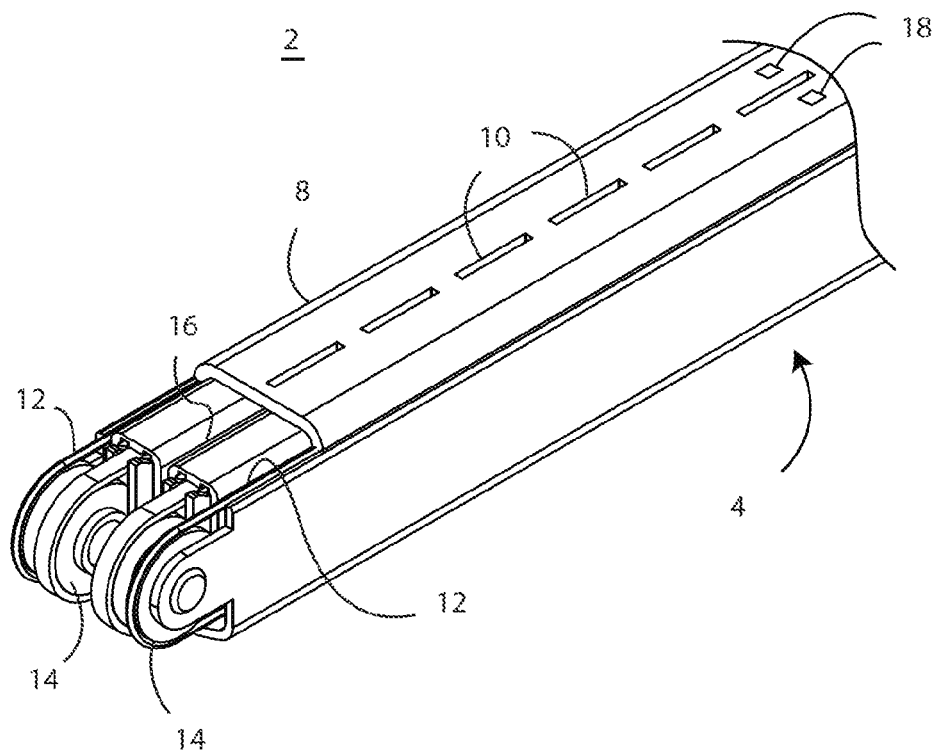
FIG. 2 is a cutaway view of the distal end of the staple holder of FIG. 1.

Referring to FIGS. 1-2, an endocutter 2 may include a staple holder 4. In the interest of clarity and brevity, with the exception of the description provided herein, one exemplary staple holder 4 may be configured substantially as set forth in FIG. 34 and the accompanying text of U.S. application Ser. No. 12/263,171, filed Oct. 31, 2008 (the "Multi-Fire Application"), which is hereby incorporated herein by reference in its entirety. A plurality of openings 6 are shown in phantom in FIG. 1 on the upper surface of the staple holder 4, through which staples are deployed. A slidable buttress 8 is positioned on the upper surface of the staple holder 4. The buttress 8 may be substantially as wide as the staple holder 4, or may be narrower or wider if desired. The buttress 8 may be substantially flat, and the edges of the buttress 8 may curve downward slightly to conform to the shape of the upper surface of the staple holder 4. Alternately, the buttress 8 may be shaped to conform to a different shape of the upper surface of the staple holder 4. Alternately, the buttress 8 need not conform to the shape of the upper surface of the staple holder 4, in whole or in part.

The buttress 8 may be perforated substantially along its longitudinal centerline, or about a different line. The perforations 10 may be rectangular, round, oval or shaped in any other suitable manner. The buttress 8 is perforated in a manner that allows easy separation of the buttress into two separate pieces after actuation of the endocutter, as described in greater detail below. The buttress 8 may be fabricated from any suitable material, such as (but not limited to) VICRYL®, produced by Ethicon, Inc. of Somerville N.J.; DEXON®, produced by Sherwood-Davis and Geck of St. Louis, Mo.; TEFLON®, produced by E.I. DuPont de Nemours & Co. of Wilmington, Del.; GORE-TEX®, produced by W. L. Gore of Flagstaff, Ariz.; animal material such as tanned bovine pericardium; biocompatible elastomers such as ε-caprolactone glycolide; or polymers, whether resorbable or not.

The buttress 8 may be connected to at least one cable 12. Advantageously, two cables 12 are provided, one attached to the buttress 8 at or near each lateral edge thereof. Further, the buttress 8 may be attached to each cable 12 substantially along the entire length of the buttress 8, such that as each portion of the buttress 8 is deployed in tissue, the remaining portion of the buttress 8 is still attached to each cable 12. Alternately, the buttress 8 may be attached to the cable 12 only at certain discrete points along the buttress 8. Each cable 12 is partially wound around a pulley 14, which may be the same pulley as described in the Multi-Fire Application about which a feeder belt is rotated. Alternately, the pulley 14 may be a different pulley 14 that shares the same axle as the pulley about which a feeder belt is rotated. Like a feeder belt, the cable 8 is partially wound about the pulley 14, such that a portion of the cable 12 is located closer to the upper surface of the staple holder 4 than the remaining portion of the cable 12. The cable 12 may extend into the handle of the endocutter 2, such that the handle is configured to pull the lower segment of the cable 12 proximally into the handle. The handle also may be configured to tension the upper segment of the cable 12. The handle may be substantially as described in the Multi-Fire Application, and may be configured to pull the lower segment of the cable 12 proximally into the handle in the same manner and/or with the same components used to retract the lower portion of a feeder belt proximally toward the handle. Alternately, the handle may be configured to tension and/or retract the cable 12 proximally in any other suitable manner.

The buttress 8 may be long enough to be utilized with all of the groups of staples to be fired. Where the staples are configured to be fired along a particular length of staple line, such as defined by a row of openings 6, the buttress 8 may be substantially as long as that staple line length multiplied by the number of firings of which the endocutter 2 is capable. Alternately, the buttress 8 may be shorter, such as where the endocutter 2 is customized for a particular surgical procedure in which a particular number of actuations is known to be used, and in which the buttress 8 is only needed in conjunction with a subset of actuations, and those actuations occur at the beginning of the surgical procedure.

The proximal end of the buttress 8 may extend along the lumen of a shaft connected to the staple holder, and may extend as far as the handle of the endocutter 2. If so, the proximal end of the buttress 8 may be stored in any suitable manner, such as by winding about a spool, or by folding within a housing. The proximal end of the buttress 8 may be tensioned, but need not be tensioned at all times, or at all.

In use, the staple holder 4 is placed in proximity to tissue to be treated, such as described in the Multi-Fire Application. The tissue may be clamped, and the endocutter 2 is then actuated to fire a plurality of staples. As the free end of each staple moves upward through the corresponding opening 6 in the staple holder 4, that free end penetrates into and then completely through the buttress 8. Each free end of each staple then penetrates into tissue and against the anvil, such as against a corresponding staple forming pocket defined in the surface of the anvil. As that free end bends, it may once again penetrate the buttress 8, this time from the other side, either into or completely through the buttress 8.

During staple deployment, or after, a knife may slide along the slot 16, cutting tissue adjacent to the staple holder 4, as set forth in the Multi-Fire Application. The knife may cut the buttress 8 along the perforations 10, thereby separating the buttress 8 into two separate strips. Alternately, the knife cuts through tissue but does not cut through the buttress 8, and the perforations 10 are sized such that tension between the two newly-cut pieces of tissue pulls the buttress 8 apart along the line of perforations 10. The two strips of buttress 8 act to interconnect the staples along a staple line, as well as distribute the force exerted by those staples against tissue across a larger surface area, reducing the loading on that tissue. The buttress 8 may also include transverse perforations 18 that allow the particular strip of buttress 8 to more easily disengage from the segment of buttress 8 connected to the proximal end of that strip. Thus, the buttress 8 may be transversely perforated at longitudinally-spaced intervals. In this way, a distal portion of the buttress 8 is separated from a remainder of the buttress 8 after the staples have been deployed into tissue and the buttress is secured in place in tissue.

The endocutter 2 may then be reset for firing again, as described in the Multi-Fire Application. During that reset process, the lower portion of the cable or cables 12 may be tensioned and/or moved proximally toward the handle, thereby dragging the upper portion of the cable or cables 12 distally. As that upper portion moves distally, it carries the next segment of buttress 8 along with it. That segment of buttress 8 moves into position on the upper surface of the staple holder 4, covering some or all of the openings 6 as described above. The endocutter 2 may then be actuated again, substantially as described above.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A surgical method of treating tissue within the body of a patient, the method comprising:
    providing an endocutter having a staple holder and a plurality of staples, wherein a plurality, but less than all, of said staples are arranged in a firing position within said staple holder;
    engaging tissue of the patient with said staple holder;
    deploying said plurality of said staples in said firing position through a buttress and into tissue of the patient;
    disengaging said end effector from tissue of the patient;
    moving a plurality of said staples into said firing position;
    engaging tissue of the patient with said staple holder;
    advancing a segment of said buttress relative to said staple holder; and
    repeating said deploying;
    wherein said endocutter includes a pulley and a cable partially wrapped around said pulley, wherein said cable is connected to said buttress, and wherein said method further comprises tensioning said cable to perform said advancing.

2. The surgical method of claim 1, wherein said endocutter includes a knife, and wherein said method further comprises cutting said buttress longitudinally into two segments with said knife during said deploying.

3. The surgical method of claim 2, wherein said cutting occurs along a perforation in said buttress.

4. The surgical method of claim 1, wherein said buttress is transversely perforated at longitudinally-spaced intervals, and wherein said method further comprises separating a distal portion of said buttress from a remainder of said buttress along said transverse perforations after said deploying.

* * * * *